United States Patent
Huang et al.

(10) Patent No.: US 6,432,088 B1
(45) Date of Patent: Aug. 13, 2002

(54) SAFETY SYRINGE WITH A NEEDLE SLEEVE LOCK

(75) Inventors: Wu-Shun Huang; Chung-Jen Lee, both of Taipei (TW)

(73) Assignee: Wu-Shun Huang, Taipei (TW)

(*) Notice: Subject to any disclaimer, the term of this patent is extended or adjusted under 35 U.S.C. 154(b) by 191 days.

(21) Appl. No.: 09/588,321

(22) Filed: Jun. 6, 2000

(51) Int. Cl.[7] .................................. A61M 5/32
(52) U.S. Cl. ................. 604/195; 604/110; 604/192; 604/197; 604/263; 128/919
(58) Field of Search .................... 604/110, 181, 604/187, 188, 192, 195, 198, 163, 197, 218, 228, 235, 239–243, 263, 264; 128/919

(56) References Cited

U.S. PATENT DOCUMENTS

| | | | | |
|---|---|---|---|---|
| 3,703,174 A | * | 11/1972 | Smith | 221/278 |
| 4,898,589 A | * | 2/1990 | Dolgin et al. | 604/110 |
| 5,047,016 A | * | 9/1991 | Dolgin et al. | 604/110 |
| 5,195,985 A | * | 3/1993 | Hall | 604/110 |
| 5,344,404 A | * | 9/1994 | Benson | 604/110 |
| 5,366,447 A | * | 11/1994 | Gurley | 604/192 |
| 5,569,203 A | * | 10/1996 | Chen | 604/110 |
| 5,899,887 A | * | 5/1999 | Liu | 604/110 |
| 6,033,385 A | * | 3/2000 | Liu | 604/110 |

* cited by examiner

Primary Examiner—Sharon Kennedy
Assistant Examiner—Michael M Thompson
(74) Attorney, Agent, or Firm—Rosenberg, Klein & Lee

(57) ABSTRACT

A safety syringe with a needle sleeve lock is provided. The needle sleeve lock is put around a cap of the syringe with radially outward projected second stoppers at rear end of the cap located between a shoulder portion and two radially inward projected first stoppers inside the needle sleeve lock, such that the cap, a hub tightly fitted in the cap, and the needle sleeve lock together form a needle sleeve lock assembly, which allows the hub to temporarily locate closely before a neck portion of a barrel of the syringe, so that the syringe may be sterilized under high temperature without stress deformation and thermal deformation. When the cap is turned to separate the second stoppers on the cap from the first shoulder portion and the first stoppers of the needle sleeve lock and then depressed, the hub and a cannula held thereto are caused to move backward and be stably retained to the neck portion of the barrel in an airtight relation. And when the cap is pulled forward again, it brings the needle sleeve lock to together separate from the hub to expose the cannula for injection.

3 Claims, 10 Drawing Sheets

SAFETY SYRINGE WITH A NEEDLE SLEEVE LOCK

BACKGROUND OF THE INVENTION

In the medical practices of early days, a used syringe would be thoroughly sterilized for repeated use later. Any incomplete sterilization would dangerously cause a second time infection of a patient and/or any other people. To avoid such second time infection, disposable syringes are largely produced. However, large amount of discarded disposable syringes also bring us new problems of environmental pollution and safety of syringes in use. This is because no specific measures have been taken in disposing cannulas of the discarded syringes and exposed cannulas tend to easily stab nursing or cleaning personnel and result in even more infected people. To prevent discarded syringes and/or cannulas from unexpectedly stabbing and therefore undesirably injuring and infecting other people, including nursing and cleaning persons, many safety syringes are particularly developed, such as U.S. Pat. Nos. 5562,627; 5,405,327; 5,569,203; 5,899,887; 5,395,346, etc., all disclose syringes having specially associated hubs and barrels, so that hubs and cannulas held thereto of used syringes can be pulled back into the barrels without the risk of unexpectedly stabbing other people.

However, all these safety syringes of prior art developed to improve conventional syringes have a common issue, that is, the hubs of these safety syringes must be able to be stably connected to the barrels and be pulled back into the latter after the syringes have been used, while the hubs must be connected to the barrels in an absolutely airtight relation that is a very important factor in providing good quality safety syringes. As it is known that, when such safety syringes are assembled in the manufacturing process thereof, the hubs and the barrels must first be associated with one another before the syringes are sterilized, so that the assembled syringes would not be contaminated after the sterilization due to contact of any part of the syringes. However, the assembled hubs and barrels are subject to stress deformation and thermal deformation during the sterilization under high temperature and such deformation would have adverse influence on the stable and airtight connection of the hubs to the barrels.

It is therefore tried by the inventor to develop a further improved safety syringe to eliminate the drawbacks existing in the safety syringes of prior art.

SUMMARY OF THE INVENTION

A primary object of the present invention is to provide a safety syringe with a needle sleeve lock that is particularly made to improve a conventional safety syringe with a retractable hub. The needle sleeve lock of the safety syringe of the present invention allows the syringe to be sterilized with the hub and the barrel thereof in a contacted but non-engaged state, so that no stress deformation of the syringe would occur to adversely affect the stable and airtight connection of the hub to the barrel of the syringe after the sterilization.

Another object of the present invention is to provide a safety syringe with a needle sleeve lock, so that the needle sleeve lock firmly holds the cap, the hub and the barrel together, allowing the cannula and the hub to be isolated from external environment and protected against contamination due to any external contacting of the cannula before the syringe is used to inject. The needle sleeve lock also allows easy retaining of the hub to the barrel of the safety syringe simply by depressing the cap. And, the cap can be then pulled forward again to bring the needle sleeve lock to together separate from the syringe to expose the cannula for injection.

The needle sleeve lock of the present invention is provided at an inner wall with two diametrically opposite and radially inward projected stoppers against which two radially outward projected stoppers at rear end of the cap abut, preventing the cap from being undesirably depressed to cause undesired early engagement of the hub with the barrel before the syringe is to be used for injection.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
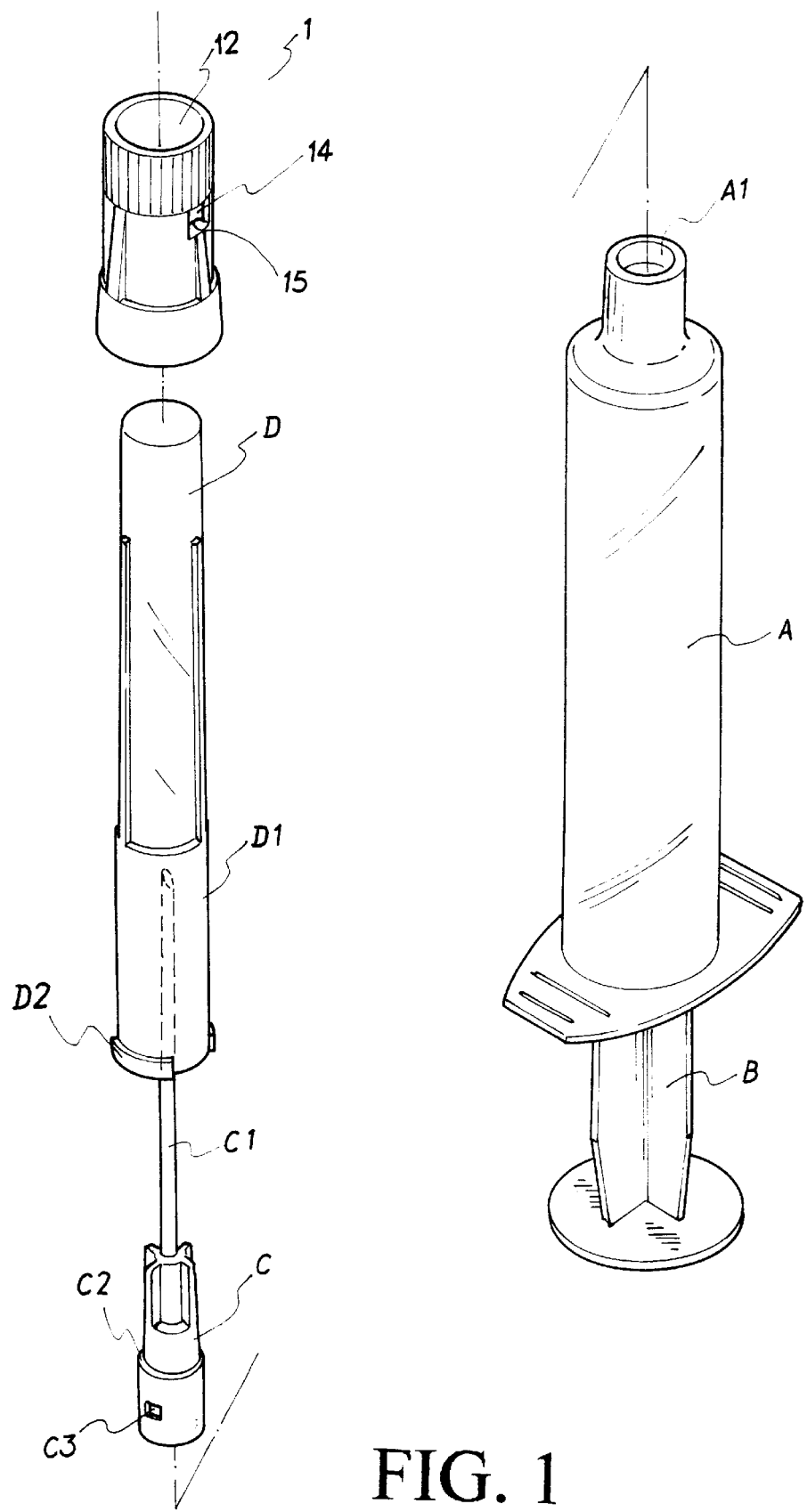
FIG. 1 is an exploded perspective of a safety syringe with a needle sleeve lock according to the present invention.

Please refer to FIG. 1 that is an exploded perspective of a safety syringe with a needle sleeve lock according to the present invention. The safety syringe mainly includes a barrel A, a plunger B slidably mounted in the barrel A, a hub C connected to a front end of the barrel A for holding a cannula Cl thereto, and a cap D for covering the cannula C1, and is characterized in a needle sleeve lock 1 put around joints of the hub C and the barrel A and of the hub C and the cap D, as can be best seen in FIG. 1. Since the barrel A, the plunger B the hub C, the cannula C1, and the cap D all are structurally similar to the conventional ones, they are not described in details herein.

Figure 2:
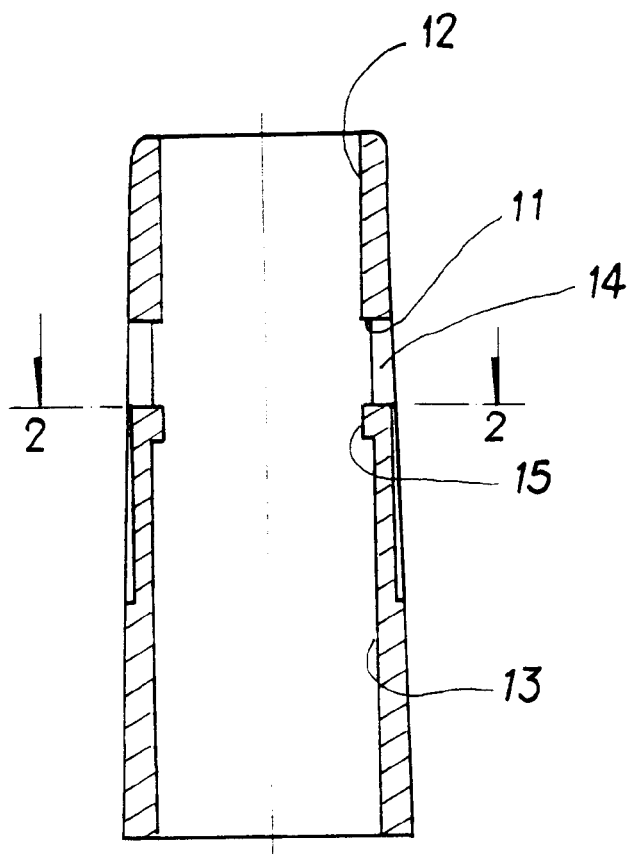
FIG. 2 is a vertical sectional view of the needle sleeve lock of the present invention.
Figure 2A:
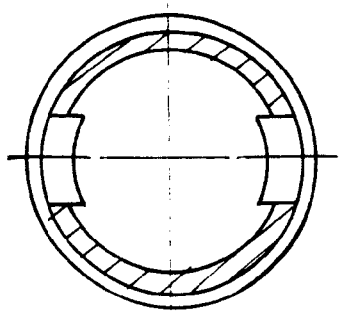
FIG. 2A is a cross sectional view of the needle sleeve lock of FIG. 2 taken on line 2—2.

Please refer to FIGS. 1, 2, and 2A. The needle sleeve lock 1 is a hollow tube defining an inner space therein. A front part of the inner space of the needle sleeve lock 1 has a reduced inner diameter. And, an inner peripheral wall 12 of this front part is properly tapered toward a front end of the safety syringe, that is, an end with the cannula C1. A rear part of the inner space of the needle sleeve lock 1 has an expanded inner diameter relative to the front part, and an inner peripheral wall 13 of the rear part is properly tapered toward the front end of the safety syringe, too. A first shoulder portion 11 is therefore formed between the inner peripheral wall 12 of the front part and the inner peripheral wall 13 of the rear part of the inner space of the needle sleeve lock 1. There are two diametrically opposite square through holes 14 formed on the rear part of the needle sleeve lock 1 immediately behind the first shoulder portion 11. Two areas on the inner peripheral wall 13 separately immediately adjacent to rear edges of the holes 14 radially project inward to form two first stoppers 15.

Figure 3:
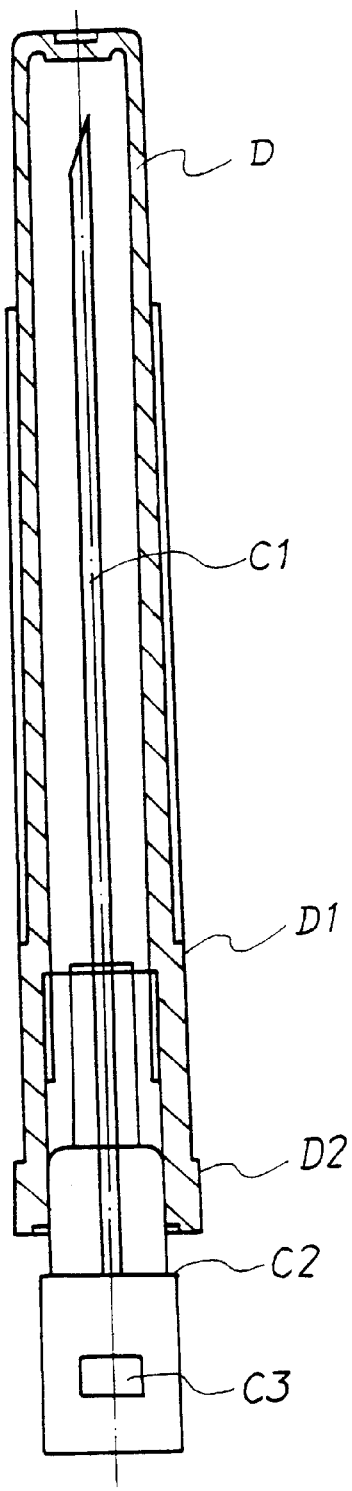
FIG. 3 is a sectional view of the hub and the cap of the safety syringe of the present invention in an assembled state.
Figure 5:
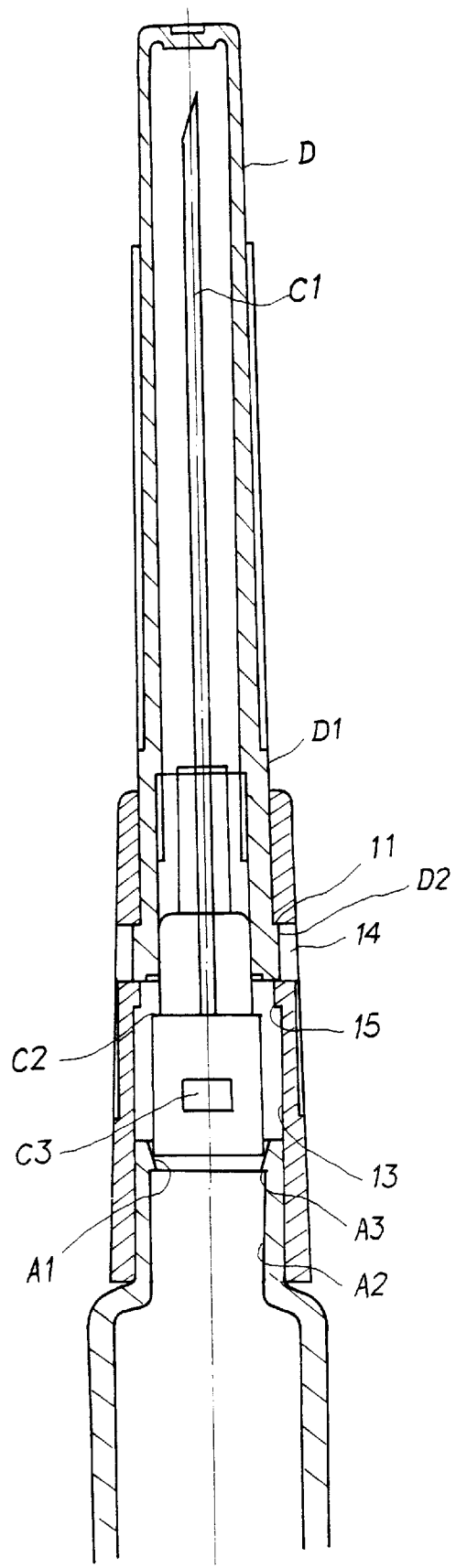
FIG. 5 is a sectional view showing the needle sleeve lock assembly of FIG. 4 being assembled to but not extended into a neck portion of a barrel of the safety syringe of the present invention.

Please refer to FIGS. 1, 3, and 5. The hub C is formed near a middle portion thereof with a second shoulder portion C2, and at a rear portion thereof with engaging holes C3. The barrel A has a diameter-reduced neck portion A2 that defines a front open end of the barrel A. An inner peripheral wall A1 of the front open end of the neck portion A2 inclines radially inward. And, a third shoulder portion A3 is formed between the inclined peripheral wall A1 and a straight inner peripheral wall of the neck portion A2 behind the inner open end of the neck portion A2. The cap D includes a slightly forward tapered outer peripheral wall surface D1, and two diametrically opposite and radially outward projected second stoppers D2 located at a rear bottom of the tapered outer peripheral wall D1.

Figure 4:
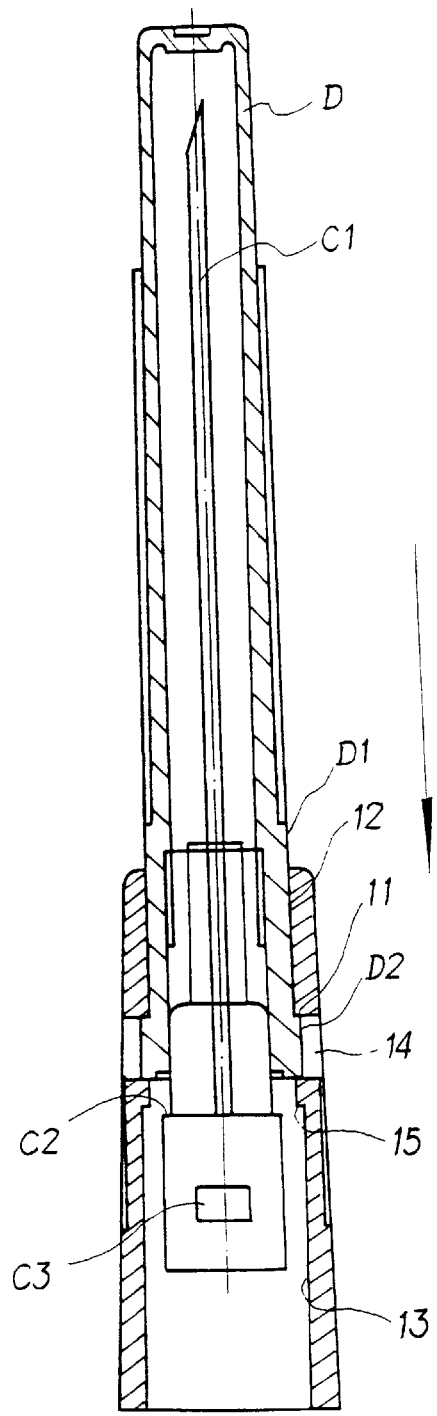
FIG. 4 is a sectional view similar to that of FIG. 3 but with the needle sleeve lock of the present invention put around the assembled hub and cap to form a needle sleeve lock assembly.

In assembling the safety syringe of the present invention, first extend the hub C and the cannula C1 connected thereto into the cap D. The cap D is so designed that it has an inner diameter similar to an outer diameter of a portion of the hub C above the second shoulder portion C2, so that the hub C could be tightly fitted in the cap D to form a needle assembly, as shown in FIG. 3. Thereafter, the needle sleeve lock 1 is put around the needle assembly from a front end of the cap D, so that the second stoppers D2 are located behind the first shoulder portion 11 inside the needle sleeve lock 1 and before the first stoppers 15, preventing the cap D from moving rearward relative to the needle sleeve lock 1. At this point, a rear end portion of the forward tapered outer peripheral wall surface D1 of the cap D fitly contacts with the front inner peripheral wall 12 of the needle sleeve lock 1 with the second stoppers D2 located between the first shoulder portion 11 and the first stoppers 15 of the needle sleeve lock 1, as shown in FIG. 4. The needle assembly and the needle sleeve lock 1 put therearound therefore form a needle sleeve lock assembly. As can be clearly seen from FIG. 4, the hub C is completely covered by the needle sleeve lock 1 and isolated from external environment and accordingly, any contamination possibly caused by undesirably contacting the cannula. The needle sleeve lock assembly is then assembled to the barrel A by engaging the inner peripheral wall 13 of the rear part of the needle sleeve lock 1 with an outer peripheral wall of the reduced neck portion A2 of the barrel A, as shown in FIG. 5, to form a syringe assembly, that is, the safety syringe of the present invention. Before being used to insect a medical liquid, this syringe assembly has a hub C that has a rear bottom portion contacting with the inclined inner peripheral wall A1 at the front open end of the neck portion A2 of the barrel A without being extended into and retained to the neck portion A2. The syringe assembly is then sterilized under high temperature in this state.

Since the hub C is not fully extended into and retained to the neck portion A2 of the barrel A when the syringe assembly is sterilized under high temperature, there would not be any stress produced at this sterilization stage. Therefore, any stress deformation and any thermal deformation of the whole syringe due to such high temperature sterilization could be avoided.

Figure 6:
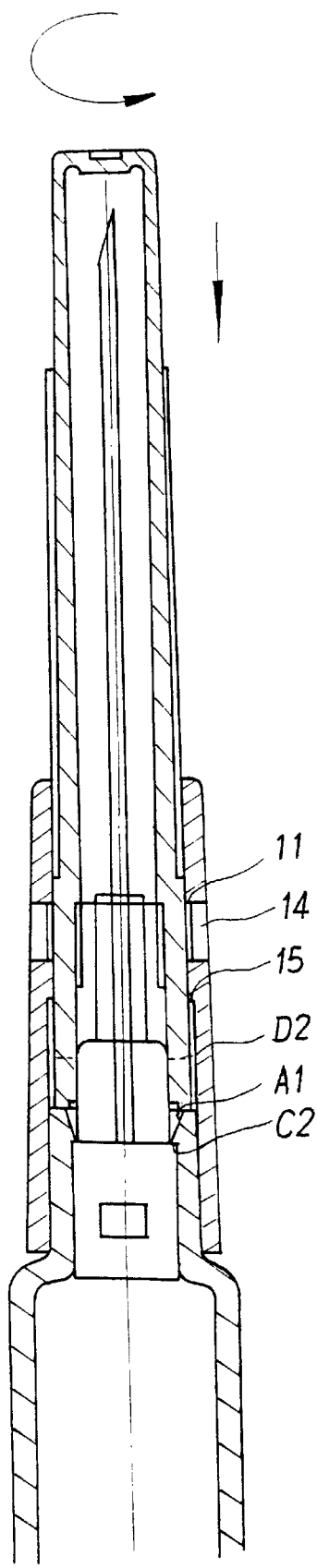
FIG. 6 is a sectional view showing the needle sleeve lock assembly of FIG. 5 being retained to the neck portion of the barrel of the safety syringe of the present invention.
Figure 7:
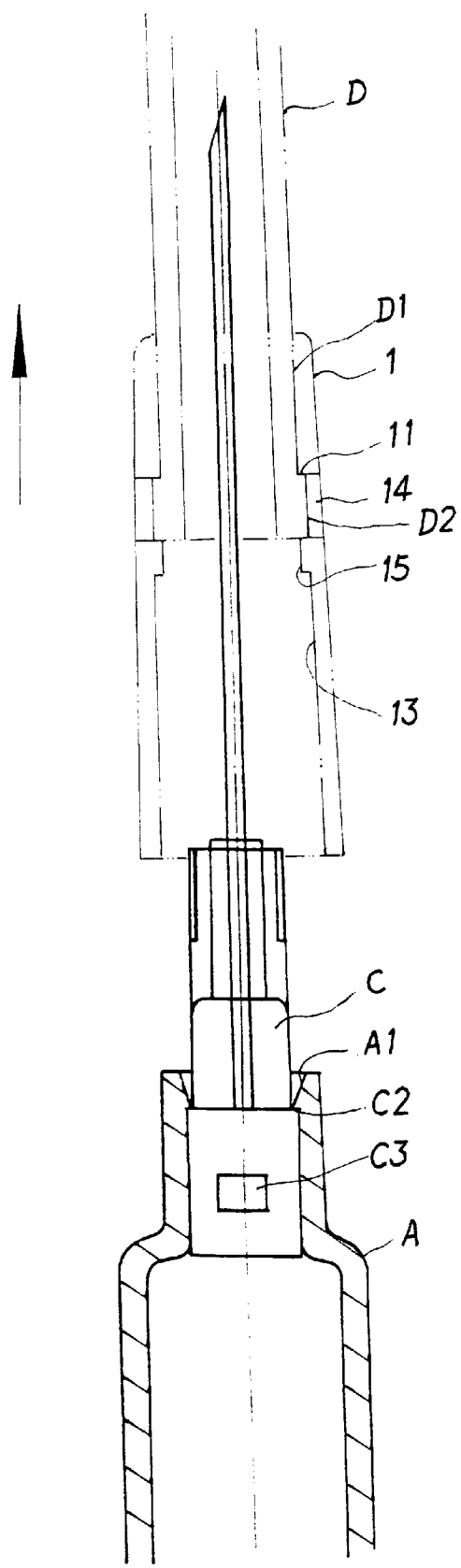
FIG. 7 illustrates the manner of removing the cap and the needle sleeve lock from the hub and the barrel of the safety syringe of the present invention.

To use the syringe assembly for injection of any medical liquid, first turn the cap D so that the second stoppers D2 thereof are moved away from their original location between the first shoulder portion 11 and the first stoppers 15. Thereafter, depress a front end of the cap D, so that the hub C tightly fitted in the cap D is brought to move downward at the same time. When the second shoulder portion C2 on the hub C is downward moved to pass through the radially inward inclined peripheral wall surface A1 and the third shoulder portion A3 at the front open end of the neck portion A2 of the barrel A, the hub C would not be able to be pulled forward again to separate from the barrel A. At this point, an outer peripheral wall surface of the rear portion of the hub C behind the second shoulder portion C2 would contact with the straight inner peripheral wall surface of the neck portion A2 behind the third shoulder portion A3 in a tight fit relation, as shown in FIG. 6, so that an airtight effect at the joint of the hub C and the barrel A is accomplished. Finally, the cap D is pulled forward to expose the cannula C1. When doing so, the second stoppers D2 on the cap D would be moved to abut against the first shoulder portion 11 inside the needle sleeve lock 1 and therefore bring the needle sleeve lock 1 to separate from the hub C at the same time, as shown in FIG. 7. Alternatively, in the event the second stoppers D2 and the first stoppers 15 are vertically aligned with one another when the cap D is forward pulled, the second stoppers D2 would abut against the first stoppers 15 to bring the needle sleeve lock 1 to separate from the hub C along with the cap D. After the cap D and the needle sleeve lock 1 have been removed to expose the cannula C1, the safety syringe of the present invention is ready for use.

Figure 8:
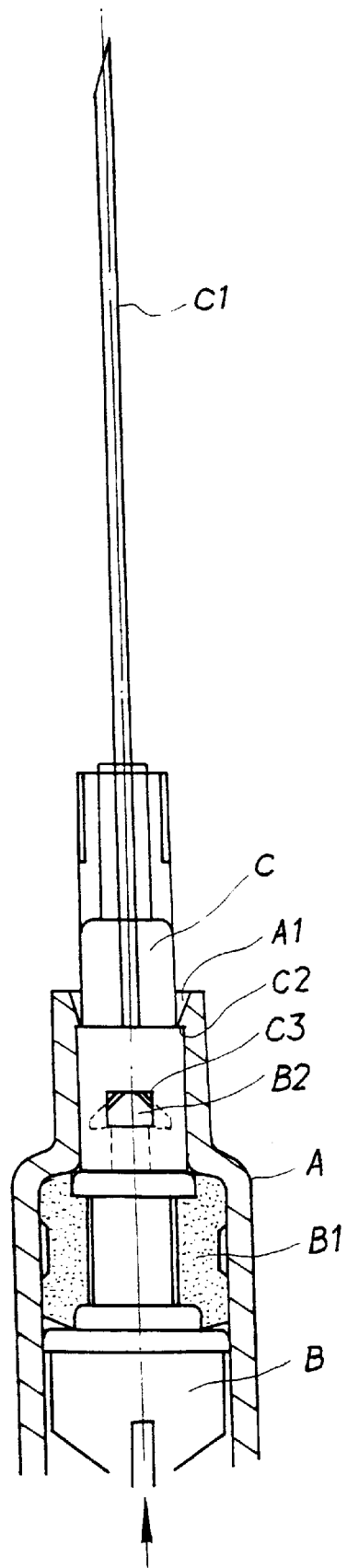
FIG. 8 shows the engagement of a plunger of the safety syringe with the hub when the plunger has been fully pushed forward in the barrel of the safety syringe.
Figure 9:
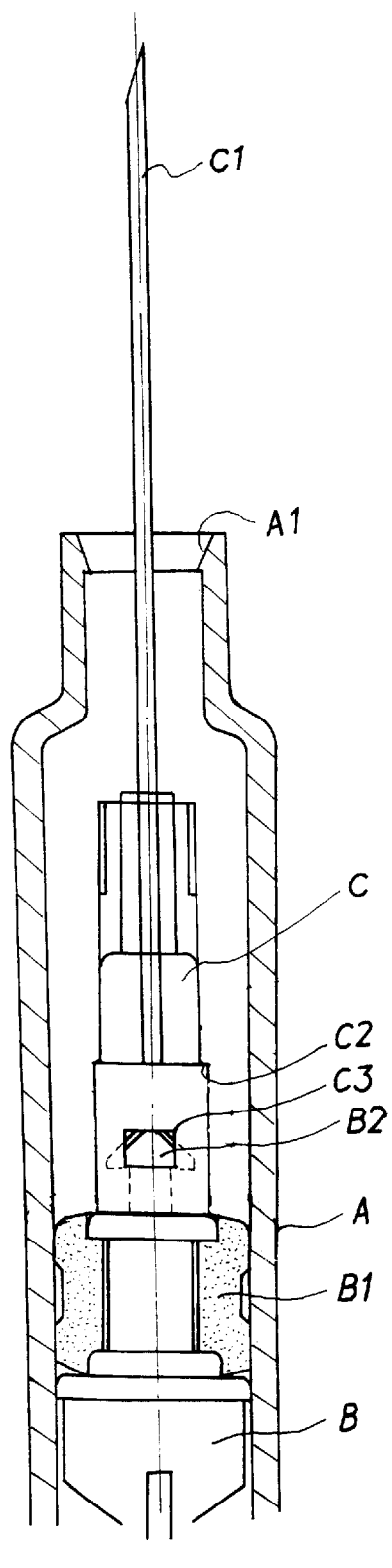
FIG. 9 shows the hub and the cannula are pulled backward by the plunger into the barrel when the cannula has been used.

When using the safety syringe of the present invention to inject a patient with medical liquid, the plunger B is fully pushed forward in the barrel A until an engaging cone B2 provided at a front end of the plunger B engages with the engaging holes C3 provided at the rear portion of the hub C, as shown in FIG. 8. After the injection, the plunger B may be pulled backward to bring the hub C, which is now associated with the plunger B, and the cannula C1, that is connected to the hub C, to move back into the barrel A, as shown in FIG. 9.

Figure 10:
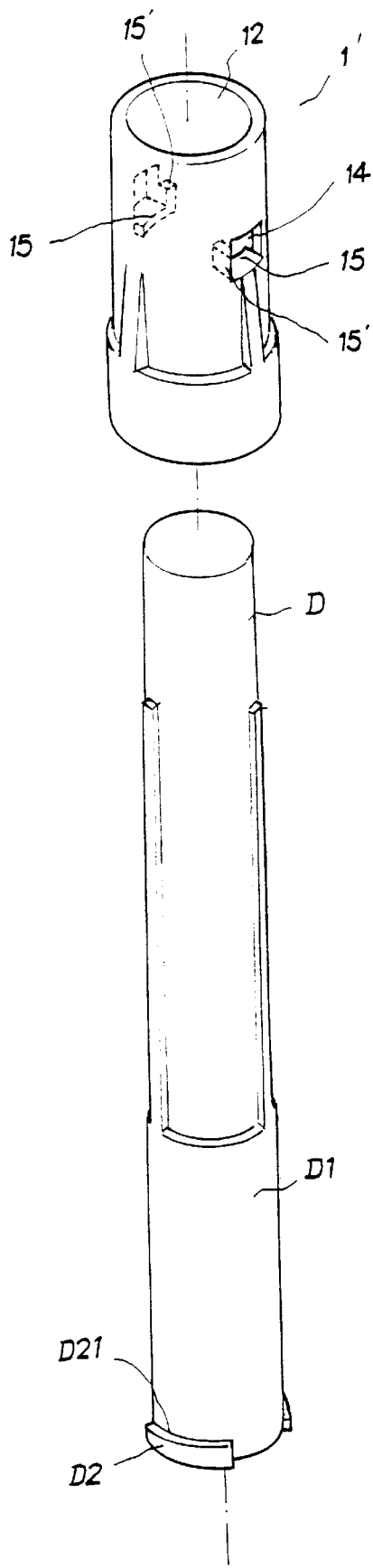
FIG. 10 shows a variant of the needle sleeve lock of the present invention.

FIG. 10 shows a needle sleeve lock 1' that is a variant of the needle sleeve lock 1. The needle sleeve locks 1 and 1' are structurally similar to each other, except that the latter includes two third stoppers 15' that separately axially extend from one end of the first stoppers 15 toward a front end of the needle sleeve lock 1', that is, an end of the needle sleeve lock 1' facing away from the barrel A. The second stoppers D2 would finally abut against the two third stoppers 15' when the cap D is turned to locate the second stoppers D2 between the first shoulder portion 11 and the first stoppers 15. The third stoppers 15' prevent the cap D from being overly turned.

As a matter of fact, the fitted contact of the forward tapered outer peripheral wall surface D1 of the cap D with the front inner peripheral wall 12 of the needle sleeve lock 1 itself enables the cap D and the needle sleeve lock 1 to stably connect to each other without the risk of becoming turnable relative to each other, unless there is an external force applied to turn them. Thus, the cap D and the needle sleeve lock 1 could still maintain their stably connected relation without the third stoppers 15'.

To enhance the stable connection of the needle sleeve lock 1 to the cap D, it is also possible to provide the first stoppers 15 and the second stoppers D2 with inclined contact surfaces between them, so that a tightness of contact of the cap D with the needle sleeve lock 1 increases with a degree of turning of the cap D relative to the needle sleeve lock 1.

In both of the above two conditions, the cap D is turned counterclockwise to separate the second stoppers D2 from the first stoppers 15. And then, the cap D may be depressed to firmly assemble the hub C to the barrel A for injection.

The following are some of the advantages of the safety syringe of the present invention:

1. The safety syringe is sterilized under high temperature before the hub C is tightly fitted into the front neck portion A2 of the barrel A. Therefore, any stress and thermal deformation at the joint of the hub and the barrel of the syringe possibly caused by such high temperature sterilization may be avoided. The safety syringe can therefore always maintain good airtightness at such joint.

2. The needle sleeve lock 1 protects the hub C and the barrel A of the safety syringe against any contamination due to undesirable contact of the hub before use.

The safety syringe with a needle sleeve lock of the present invention is therefore superior to the conventional safety syringes and is practical for use.

What is claimed is:

1. A safety syringe with a needle sleeve lock comprising a barrel having a diameter-reduced front neck portion, a plunger slidably mounted in said barrel, a hub located at a front end of said barrel for holding a cannula thereto, and a cap into which said hub is tightly fitted so that said cannula is protectively covered by said cap, said safety syringe being characterized in a needle sleeve lock that is put around joints of said hub and said neck portion of said barrel and of said hub and said cap;

said needle sleeve lock being a hollow tube defining is an inner space therein, a front part of said inner space of said needle sleeve lock having a reduced inner diameter, and an inner peripheral wall of this front part being tapered toward a front end of said safety syringe, that is, an end with said cannula, and a rear part of said inner space of said needle sleeve lock having an expanded inner diameter relative to said front part, and an inner peripheral wall of the rear part also being tapered toward the front end of said safety syringe, so that a first shoulder portion is formed between said inner peripheral wall of said front part and said inner peripheral wall of said rear part of said inner space of said needle sleeve lock ; two diametrically opposite square through holes being formed on said rear part of said needle sleeve lock immediately behind said first shoulder portion, and areas on said inner peripheral wall separately immediately adjacent to rear edges of said two square through holes radially projecting inward to form two first stoppers;

said needle sleeve lock being put around said hub and said cap from a front end of said cap, so that two radially outward projected second stoppers at a rear end of said are located between and abut on said first shoulder portion inside said needle sleeve lock and said first stoppers inside said needle sleeve lock to separately extend into the two square through holes to form a needle sleeve lock assembly, said needle sleeve lock being assembled to said diameter-reduced neck portion of said barrel with a part of said inner peripheral wall surface of said rear part of said needle sleeve lock contacting with an outer peripheral wall of said diameter-reduced neck portion of said barrel in a tight fit relation, allowing said hub to locate closely before a front open end of said neck portion without being extended into said neck portion; whereby when said cap is turned to move said second stoppers away from positions between said first shoulder portion and said first stoppers on said needle sleeve lock and then depressed, said hub tightly fitted in said cap is brought to move backward into said neck portion of said barrel and be retained thereto by a second shoulder portion inside said neck portion, and when said cap is pulled forward again and said second stoppers on said cap abut against said first shoulder portion inside said needle sleeve lock in the case said second stoppers are not axially aligned with said first stoppers, or against said first stoppers in the case said second stoppers are axially aligned with said first stoppers, said needle sleeve lock along with said cap are removed from said hub to expose said cannula for injection.

2. A safety syringe with a needle sleeve lock as claimed in claim 1, wherein said two first stoppers are provided at their one end each with an axially and forward extended third stoppers, against which one end of said two second stoppers on said cap abut, so that said cap is prevented from being overly turned relative to said needle sleeve lock.

3. A safety syringe with a needle sleeve lock as claimed in claim 1, wherein said first and said second stoppers have inclined contact surfaces between them to allow tight contact with one another through turning said cap relative to said needle sleeve lock.

* * * * *